US00PP25974P3

(12) United States Plant Patent
Heims

(10) Patent No.: US PP25,974 P3
(45) Date of Patent: Oct. 6, 2015

(54) ***BEGONIA* PLANT NAMED 'FIRST BLUSH'**

(50) Latin Name: *Begonia rex-cultorum*
Varietal Denomination: First Blush

(71) Applicant: Terra Nova Nurseries, Inc., Canby, OR (US)

(72) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 118 days.

(21) Appl. No.: 13/987,818

(22) Filed: Sep. 5, 2013

(65) Prior Publication Data

US 2015/0067936 P1 Mar. 5, 2015

(51) Int. Cl.
*A01H 5/02* (2006.01)

(52) U.S. Cl.
USPC ..... Plt./343
CPC ..... *A01H 5/0238* (2013.01)

(58) Field of Classification Search
USPC ..... Plt./343
See application file for complete search history.

(56) References Cited

PUBLICATIONS

American Nurseryman Magazine, Feb. 1, 2013.*

* cited by examiner

*Primary Examiner* — Keith Robinson
(74) *Attorney, Agent, or Firm* — Klarquist Sparkman, LLP

(57) ABSTRACT

A new and distinct form of *Begonia* plant characterized by broad leaves colored silver with a dark star-shape at the leaf base that is surrounded by a purple blush, maroon leaf backs, a bushy habit, light pink flowers in winter to early spring, tolerant of cool temperatures to 33° F., and excellent vigor.

1 Drawing Sheet

Botanical denomination: *Begonia rex-cultorum.*
Variety designation: 'First Blush'.

BACKGROUND OF THE INVENTION

The present invention relates to a new and distinct cultivar of *Begonia*, of the family Begoniaceae, and given the cultivar name, 'First Blush'. The new cultivar originated from a cross between unknown *Begonia rex-cultorum* parents. This selection is uniquely characterized by:

1. broad leaves colored silver with a dark star-shape at the leaf base that is surrounded by a purple blush,
2. maroon leaf backs,
3. a bushy habit,
4. light pink flowers in winter to early spring,
5. tolerant of cool temperatures to 33° F., and
6. excellent vigor.

Compared to *Begonia* 'Raspberry Swirl', an unpatented plant, the new cultivar has leaves that are flatter and not swirled, with a larger silver area and a larger star pattern at the leaf base.

Compared to *Begonia* 'Fireworks', an unpatented plant, the new cultivar has leaves that are less rugose, darker silver colored, the star pattern is smaller and does not go into the veins to the leaf margins, and the blush is around the star pattern rather than the leaf margin.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'First Blush'.

FIG. 2 shows a 1 and-a-half year old plant in a growing in a one gallon container in February in Canby. Oreg.

DETAILED PLANT DESCRIPTION

The following is a detailed description of the new *Begonia* cultivar based on observations of nine-month-old specimens grown in one gallon containers in a cool greenhouse in early January in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type.*—Herbaceous rhizomatous perennial.
*Form.*—Clumping, caulescent.
*Cold hardiness.*—USDA Zone 10a.
*Size.*—Grows to 36 cm tall and 40 cm wide.
*Vigor.*—Excellent.
*Roots and rooting.*—Roots appear on leaf cuttings in 2 weeks; fine, fibrous, and white in color.

Stem:

*Type.*—Upright.
*Size.*—Grows to 10 cm long and 25 mm wide.
*Lateral branches.*—None.
*Internodes.*—From 7 mm to 1 cm long.
*Surface.*—Pubescent.
*Color.*—Brown 200B.

Leaf:

*Type.*—Simple.

*Arrangement.*—Alternate, congested.

*Number.*—About 60.

*Shape.*—Broadly ovate to orbicular.

*Margins.*—Undulate, coarsely senate, sometimes with larger teeth (to 9 mm long).

*Apex.*—Acute to acuminate.

*Base.*—Oblique.

*Venation.*—Palmate, Brown 200A on topside with the star pattern, bottom side Red Purple 59A.

*Blade size.*—Grows to 20 cm wide and 19 cm long.

*Surface texture.*—Pubescent on top and glabrous on bottom.

*Stipules.*—Deciduous, ovate-lanceolate, 30 mm long and 9 mm wide, apex acuminate and cuspidate, base clasping, entire, back side pubescent, inside glabrous, both sides Red Purple 61A.

*Petiole description.*—Grows to 17 cm long and 8 mm wide, succulent, pubescent, Greyed Purple 187A.

*Leaf color.*—Top side closest to Greyed Green 188B where silver, tinted Red Purple 59B, star pattern Black 202A; bottom side Purple 59A at bottom ⅓ and the rest Greyed Green 189B heavily tinted Purple 59A.

Inflorescence:

*Type.*—Axillary, bisexual, cymose.

*Number of flowers per cyme.*—About 4.

*Peduncle description.*—Grows 9 cm to 19 cm long and 2 mm to 4 mm wide, glabrous, fleshy, slightly arching, Greyed Purple 187C; with 2 opposite, dehiscent petiolate leaf-bracts below each cyme, which grow to 6 mm wide and 17 mm long, margins entire, tip apiculate, back side sparsely pubescent, inside glabrous, both sides Greyed Red 184C.

*Pedicel description.*—Grow to 25 mm long, 1.5 mm wide, fleshy, glabrous, slightly arching, Red Purple 63D on staminate flowers, Greyed Purple 185B on pistillate flowers.

*Bloom period.*—Late fall to early winter in Canby, Oreg.

Flower bud:

*Size.*—Staminate flowers 9 mm long and 6 mm wide prior to opening; pistillate flowers are 15 mm deep and 16 mm wide prior to opening.

*Description.*—Ovoid, pubescent.

*Color.*—Red Purple 59D on tepal area and ovary.

Flower:

*Type.*—Monoecious, bilaterally symmetrical.

*Pistillate flower.*—Grows to 23 mm deep and 40 mm wide overall; 5 fleshy tepals, grow to 18 mm long and 16 mm wide, broadly elliptical, tip and base obtuse, margins entire, glabrous on inside and pubescent on outside, tepals Red Purple 65B on inside and 65A and 65B on outside; pistil 1, 18 mm long, ovary to 30 mm wide and 12 mm deep, three winged, two equal and one longer, Greyed Purple 182A, style 3 mm long and Yellow 13B, stigma 2 to 3 branched and twisted, stigma 6 mm deep and 10 mm wide overall, Green Yellow 1C.

*Staminate flower.*—12 mm deep and 33 mm wide, 4 tepals, 2 larger outer tepals 16 mm long and 15 mm wide, cupped, broadly elliptical, margin entire, tip obtuse, base truncate, Red Purple 65A inside and 63C outside; inner tepals grow to 13 mm long and 9 mm wide, oblong, entire, tip obtuse, base attenuate, both sides Red Purple 65A; stamen many in a globular head 7 mm in diameter, filament 2 mm long, anthers 1.5 mm long and Green Yellow 1D, anthers and pollen Yellow 8C. Texture of inner and outer tepals of the staminate flower is satiny.

*Fragrance.*—None.

*Lastingness.*—A cyme blooms for about 4 weeks on the plant; flowers are self-cleaning.

Fruit and seed: None, sterile.

Diseases and pests: The new cultivar is typical to the genus. No problems have been found in Canby, Oreg.

I claim:

1. A new and distinct *Begonia* plant as hereby illustrated and described.

* * * * *

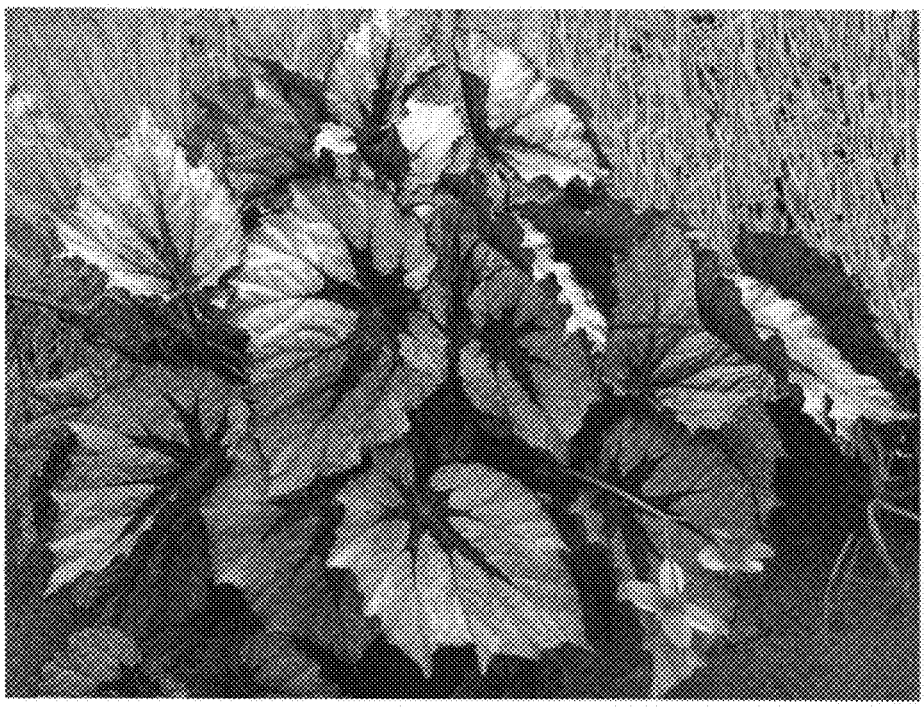

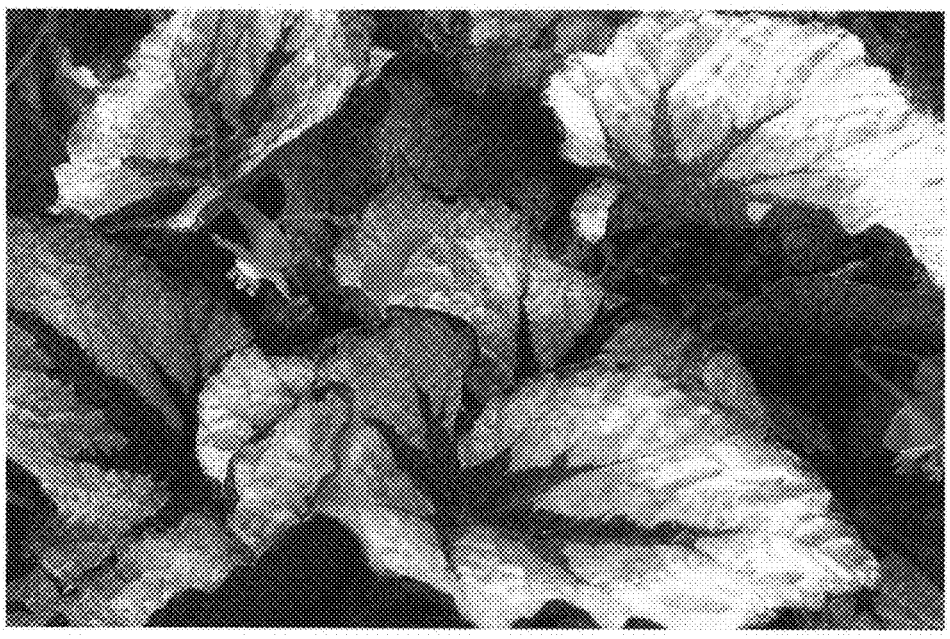
FIG. 1 above, FIG. 2 below